US00PP25350P2

(12) United States Plant Patent
Lentjes

(10) Patent No.: US PP25,350 P2
(45) Date of Patent: Mar. 17, 2015

(54) ***CHELONE* PLANT NAMED 'ARMITPP02'**

(50) Latin Name: *Chelone lyonii*
Varietal Denomination: Armtipp02

(71) Applicant: Gerardus Bernard Maria Lentjes, Kerkdriel (NL)

(72) Inventor: Gerardus Bernard Maria Lentjes, Kerkdriel (NL)

(73) Assignee: Armada International BV, De Lier (NL)

( * ) Notice: Subject to any disclaimer, the term of this patent is extended or adjusted under 35 U.S.C. 154(b) by 143 days.

(21) Appl. No.: 13/694,261

(22) Filed: Nov. 13, 2012

(51) Int. Cl.
*A01H 5/00* (2006.01)

(52) U.S. Cl.
USPC ..... Plt./263.1

(58) Field of Classification Search
CPC ..... A01H 5/02; A01H 5/00
USPC ..... Plt./263.1
See application file for complete search history.

*Primary Examiner* — June Hwu
(74) *Attorney, Agent, or Firm* — Penny J. Aguirre

(57) ABSTRACT

A new cultivar of *Chelone* named 'Armtipp02', characterized by its sturdy stems that are held upright, its large flowers that are dark pink in color, its foliage that is dark green and matures to a blend of dark green and black, and its numerous flowers per stem with blooms commencing early in the season.

2 Drawing Sheets

Botanical classification: *Chelone lyonii.*
Varietal denomination: 'Armtipp02'.

BACKGROUND OF THE INVENTION

The present invention relates to a new and distinct cultivar of *Chelone* plant, botanically known as *Chelone lyonii* 'Armtipp02' and will be referred to hereinafter by its cultivar name, 'Armtipp02'.

'Armtipp02' was derived from a controlled breeding program conducted by the Inventor in a nursery in De Lier, The Netherlands. 'Armtipp02' was selected in July of 2010 by the Inventor as a single unique plant derived from a cross made in July of 2009 between an unnamed plant of *Chelone lyonii* as the female parent and an unnamed plant of *Chelone lyonii* from the Inventor's breeding program, identified with accession No. 1225, as the male parent.

Asexual propagation of the new cultivar was first accomplished by stem cuttings by the Inventor in Kerkdriel, the Netherlands in July of 2010. Propagation by stem cuttings has determined that the characteristics of this cultivar are stable and are reproduced true to type in successive generations.

SUMMARY OF THE INVENTION

The following traits have been repeatedly observed and represent the characteristics of the new cultivar as grown in De Lier, The Netherlands. These attributes in combination distinguish 'Armtipp02' as a unique cultivar of *Chelone.*

1. 'Armtipp02' exhibits sturdy upright stems.
2. 'Armtipp02' exhibits large flowers that are dark pink in color.
3. 'Armtipp02' exhibits foliage that is dark green and matures to a blend of dark green and black.
4. 'Armtipp02' exhibits numerous flowers per stem with blooms commencing early in the season.

The female parent and typical plants of *Chelone lyonii* differ from 'Armtipp02' in having less flowering stems, lighter pink flowers, weaker stems and in being taller in height. The male parent differs from 'Armtipp02' in having weaker stems and flowers that are smaller and lighter pink in color. 'Armtipp02' can be compared to the cultivar 'Hot Lips' (not patented). 'Hot Lips' is similar to 'Armtipp02' in having drak green foliage that is tinged with black and in having deep pink flowers, but differs from 'Armtipp02' in having stems that are red in color most of the season.

BRIEF DESCRIPTION OF THE PHOTOGRAPHS

The plants and plant parts in the photographs were taken of a two year-old plant of 'Armtipp02' as grown outdoors in a 17-cm container in Kerdriel, The Netherlands.

Figure 1:
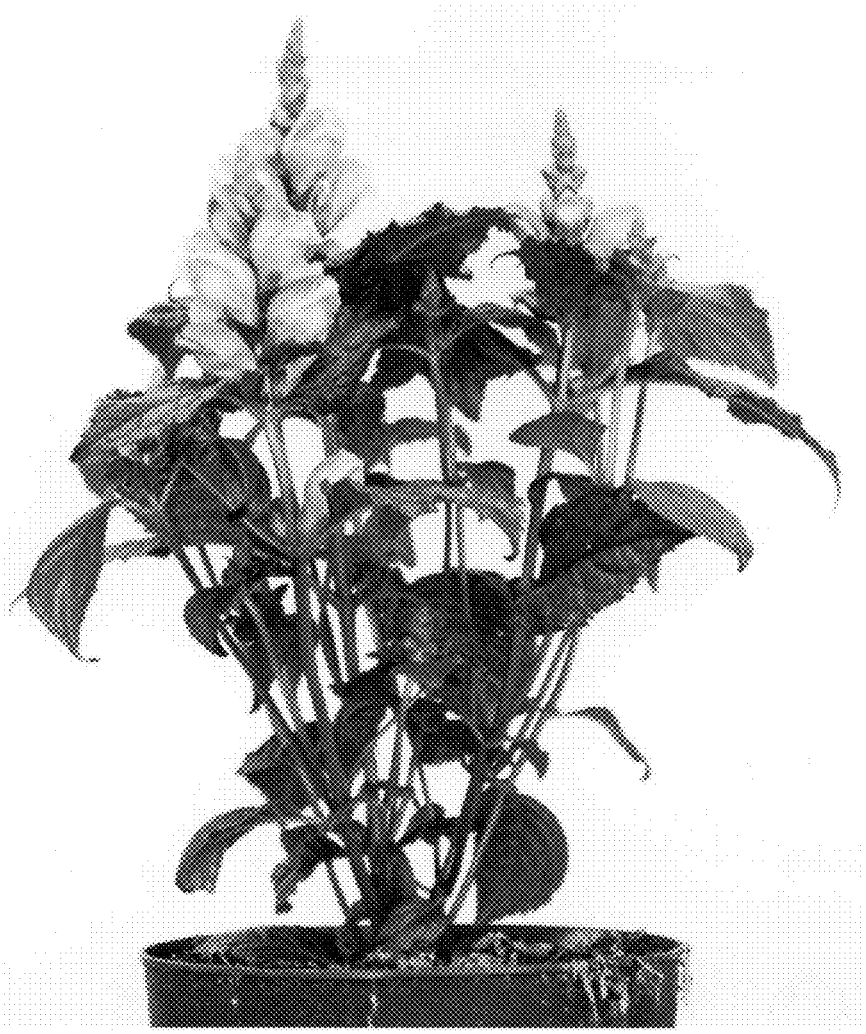

The photograph in FIG. 1 provides a side view of 'Armtipp02' in bloom.

Figure 2:
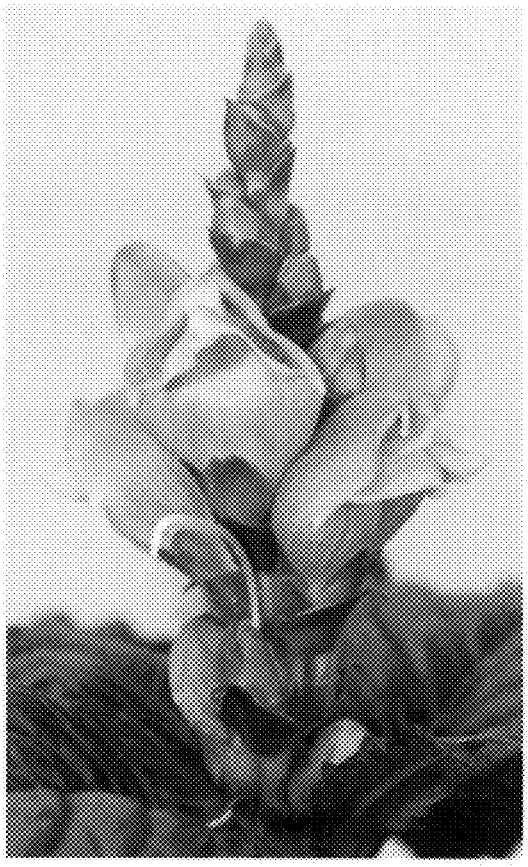

The photograph in FIG. 2 is a close-up view of the flowers of 'Armtipp02'.

Figure 3:
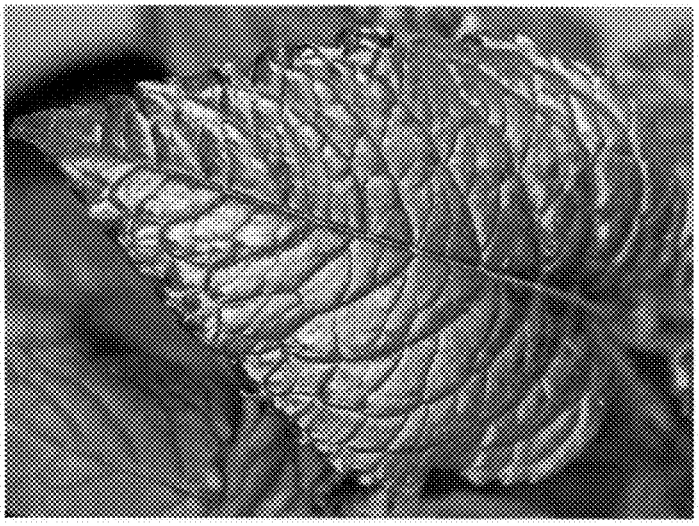

The photograph in FIG. 3 is a close-up view of a mature leaf of 'Armtipp02'.

The colors in the photographs may differ slightly from the color values cited in the detailed botanical description, which accurately describe the colors of the new *Chelone.*

DETAILED BOTANICAL DESCRIPTION

The following is a detailed description of 2 year-old plants of the new cultivar as grown outdoors in 17-cm pots in Kerdriel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from mid-summer to early autumn in The Netherlands, early blooming for the species.

*Plant type.*—Herbaceous perennial.

*Plant habit.*—Clump-forming, upright, and well-branched.

*Height and spread.*—Average of 32.5 cm in height and an average of 26.5 cm in spread.

*Hardiness.*—At least hardy to U.S.D.A. Zone 4.

*Diseases.*—No unique susceptibility or resistance to diseases has been observed.

*Root description.*—Fibrous.

Growth and propagation:

*Propagation.*—Stem cuttings.

*Growth rate.*—Moderately vigorous.

Stem description:

*Stem shape.*—Round.

*Stem color.*—146A, tinged with N186C towards the base.

*Stem size.*—Average of 18.3 cm in length and 3.5 mm in diameter.

*Stem surface.*—Moderately glossy and sparsely covered with very short hairs, average length is 0.3 mm and 157D in color.

*Stem strength.*—Sturdy.

*Stem aspect.*—Held upright to an average angle of 22° to vertical.

*Internode length.*—Average of 6.7 cm.

*Branching habit.*—Stems arise from base, an average of 14 branches.

Foliage description:

*Leaf shape.*—Ovate.

*Leaf division.*—Simple.

*Leaf base.*—Attenuate.

*Leaf apex.*—Apiculate.

*Leaf venation.*—Pinnate, color of upper surface 143B, color of lower surface 144B.

*Leaf margins.*—Serrate.

*Leaf attachment.*—Petiolate.

*Leaf arrangement.*—Opposite.

*Leaf surface.*—Upper and lower surface; smooth, glossy and rugose.

*Leaf color.*—Young upper surface; N137C, young lower surface; 138A, mature upper surface; a color between N189A and 202A, mature lower surface; between 147A and 189A.

*Leaf number.*—An average of 6 leaves (3 pairs) per lateral branch.

*Leaf size.*—Average of 8.5 cm in length and 5 cm in width.

*Petiole.*—Average of 1.3 cm in length, 0.3 cm in diameter, color; upper surface 143A in color, lower surface 144A in color, glabrous surface.

Flower description:

*Inflorescence type.*—Terminal raceme.

*Inflorescence size.*—Average of 9.1 cm in height and 5.7 cm in width.

*Flower type.*—Single, bilabiate, consisting of two upper petal lobes and three lower petal lobes.

*Flower fragrance.*—None.

*Flower lastingness.*—Up to seven days, within a raceme the lowest flowers open first, followed by the flowers upward in the raceme, self-cleaning.

*Flower bud description.*—Obovate in shape, average of 2.6 cm in length and 1 cm in diameter, color; a color between 77C and N77B and 76C and 76D near calyx and slightly suffused with 144A to 144B at the apex prior to opening, calyx portion 143A and blending to 143C at the base.

*Flower quantity.*—Average of 28 per inflorescence, about 200 per plant as grown in a 17-cm container.

*Flower aspect.*—Held outward-slightly upward.

*Flower size.*—3.5 cm in depth, 2.2 cm in diameter.

*Peduncle description.*—About 7.5 cm in length and 4 mm in width, strong, 143C in color, glabrous surface.

*Pedicels.*—None, flowers are sessile to peduncle.

*Petals.*—5 with 2 comprising upper petal lobes and 3 comprising lower petal lobes, narrow obovate in shape, 60% of lower portion is fused, free parts have entire margins, an average of 3.1 cm in length and 2.2 cm in width, apex of upper and lower petal lobes acute, upper and lower surface is smooth and slightly glossy on all petals, color of outer surface (opening and fully open); upper and lower petals 77C to 77D, color of inner surface (opening and fully open); upper petals between 72B and 77B with a bearded palate 11A in color, lower petals 77C.

*Corolla tube* (*below fused base of petals*).—An average of 7 mm in length and 3 mm in width and 145D in color on inner and outer surfaces, glabrous on inner and outer surface.

*Calyx.*—Rotate in shape, 10 mm in length and 8 mm in diameter.

*Sepals.*—5, rotate, spirally placed on receptacle, ovate to oblong in shape with entire margin and obtuse apex, base is broad cuneate, surface is smooth and slightly glossy, average of 9 mm in length and 6 mm in width, color of young upper and lower surfaces; 143A and blending to 143C at the base, color of mature upper and lower surfaces; 141A to 141B and blending to 143B to 143C at the base.

*Staminodes.*—Present in each flower, implanted in the base of the upper petal, 1.2 cm in length and 8 mm in width, 73B to 73D in color, glabrous on upper and lower surface, irregular in shape, base cuneate and apex obtuse.

*Bracts.*—2, broadly ovate in shape, 147A in color on upper and lower surface, an average of 1 cm in length and wide, base clasping, margins entire, apex acute to acuminate, both surfaces glabrous with ciliate margins.

Reproductive organs:

*Gynoecium.*—1 Pistil about 2.8 cm in length, stigma is club-shaped and NN155D in color, style is about 2.7 cm in length, and NN155D in color, ovary is 143A in color.

*Androcoecium.*—4 stamens, filaments are 2.3 cm in length and NN155C to NN155D in color and densely covered with pubescent hairs 11A in color and becoming NN155D in color at the base of the hairs, anthers are 0.3 cm in width and N200A in color and moderately covered with short hairs 156D in color, pollen is low in quantity and about 156D in color.

*Fruit/seed.*—None produced to date.

It is claimed:

1. A new and distinct cultivar of *Chelone* plant named 'Armtipp02' as herein illustrated and described.

* * * * *